United States Patent [19]

Wang et al.

[11] Patent Number: 5,598,005
[45] Date of Patent: Jan. 28, 1997

[54] NON-DESTRUCTIVE METHOD FOR DETERMINING THE EXTENT OF CURE OF A POLYMERIZING MATERIAL AND THE SOLIDIFICATION OF A THERMOPLASTIC POLYMER BASED ON WAVELENGTH SHIFT OF FLUROESCENCE

[75] Inventors: Francis W. Wang, Gaithersburg, Md.; Robert E. Lowry, Falls Church, Va.; King-Fu Lin, Taipei, Taiwan

[73] Assignee: The United States of America as represented by the Secretary of the Commerce, Washington, D.C.

[21] Appl. No.: 389,823

[22] Filed: Feb. 15, 1995

[51] Int. Cl.$^6$ .............. G01N 21/64; G01N 33/44
[52] U.S. Cl. .................. 250/459.1; 250/458.1
[58] Field of Search ................ 250/458.1, 459.1

[56] References Cited

U.S. PATENT DOCUMENTS

| | | |
|---|---|---|
| 4,651,011 | 3/1987 | Ors et al. . |
| 4,717,545 | 1/1988 | Morris . |
| 4,945,245 | 7/1990 | Levin ................ 250/459.1 X |
| 5,047,444 | 9/1991 | DeVoe et al. . |
| 5,100,802 | 3/1992 | Mickols ................... 436/34 |
| 5,158,720 | 10/1992 | Levy ................... 250/458.1 X |
| 5,165,972 | 11/1992 | Porter . |
| 5,377,294 | 12/1994 | Onishi et al. . |

Primary Examiner—Carolyn E. Fields
Assistant Examiner—Edward J. Glick
Attorney, Agent, or Firm—Larson and Taylor

[57] ABSTRACT

The change in the peak fluorescence wavelength of a small amount of a fluorescent compound, i.e., a fluorophore, which has been dissolved in a polymerizing material or a thermoplastic polymer is used to determine the extent of cure or solidification, respectively. The measured wavelength-shift can either be compared with a previously determined correlation to obtain an absolute value for the extent of cure, or can be utilized to compare or maintain an acceptable extent of cure throughout a manufacturing or a clinical process. Similarly, in the processing of a thermoplastic polymer by injection molding, the measured wavelength shift can either be compared with a previously determined correlation to obtain an absolute value for the temperature of the polymer, or can be utilized to adjust the injection molding cycle so that the mold is opened at the optimum times. The fluorophores used in the method are preferably selected from a class of fluorophores comprising alpha, omega substituted linear alkenes having an electron accepting group attached at the alpha position and an electron donating group attached at the omega position.

16 Claims, 3 Drawing Sheets

NON-DESTRUCTIVE METHOD FOR DETERMINING THE EXTENT OF CURE OF A POLYMERIZING MATERIAL AND THE SOLIDIFICATION OF A THERMOPLASTIC POLYMER BASED ON WAVELENGTH SHIFT OF FLUROESCENCE

FIELD OF THE INVENTION

The present invention relates to a non-destructive method for measuring the extent of cure of a polymerizing material or the extent of solidification of a thermoplastic polymer being processed by injection molding, and, more particularly, to a method which utilizes peak fluorescence wavelength to measure the extent of cure or solidification, and to a class of fluorophores for use in connection therewith.

BACKGROUND OF THE INVENTION

In the manufacture of a variety of products, such as polymer matrix composites and vinyl polymers, as well as in the applications of dental or medical resins, the cure or polymerization reactions of polymerizing materials must be adequately monitored and controlled to produce the desired resultant products. Fluorescence techniques are particularly useful for cure monitoring because they are sensitive and adaptable to non-destructive, in-line, real-time monitoring.

One known fluorescence technique for monitoring the cure of an epoxy resin is disclosed in Wang, et al., 27 *Polymer* 1529 (1986), which is herein incorporated by reference. According to the technique, a trace amount of 1-(4-dimethylaminophenyl)-6-phenyl-1,3,5-hexatriene ("DMA-DPH"), which is a viscosity-sensitive fluorophore, and a trace amount of 9,10-diphenylanthracene ("DPA"), an internal standard fluorophore which is insensitive to viscosity, are dissolved in an epoxy resin. The fluorescence intensities of the viscosity-sensitive fluorophore, DMA-DPH, and the internal standard, DPA, are then measured at various cure times. Finally, the ratio of these intensities, which is insensitive to the change in the shape of the sample or the presence of filler particles, is used to monitor the cure of the epoxy resin. An advantage of this technique is that the use of two fluorophores eliminates inaccuracies in measuring the absolute fluorescence intensity of a viscosity-sensitive fluorophore when the polymerizing material contains filler particles or undergoes polymerization shrinkage. However, the method suffers from the drawback that the two fluorophores may have overlapping fluorescence spectra, thereby necessitating complicated deconvolution of the fluorescence spectra.

U.S. Pat. No. 4,651,011 to Ors and Scarlata, also incorporated herein by reference, discloses another method of determining the extent of cure of a polymerizing material in which the change in fluorescence anisotropy of a fluorophore dissolved in a polymerizing material is measured. In contrast to the above-described method of Wang, et al., the method of Ors and Scarlata utilizes only one fluorophore. However, a major drawback of the method is that it requires the use of a complex optical system. In particular, the method uses polarized exciting radiation, together with polarizers for separating fluorescence intensities in two mutually perpendicular directions.

SUMMARY OF THE INVENTION

Thus, it is a purpose of the present invention to overcome the disadvantages of the prior art and thereby provide a relatively simple method of determining the extent of cure of a polymerizing material or the extent of solidification of a thermoplastic polymer and to provide a class of fluorophores for use in the method.

According to the method of the invention, the extent of cure of a polymerizing material or the extent of solidification of a thermoplastic polymer are measured by first dissolving a fluorophore in the polymerizing material or thermoplastic polymer. The change in peak fluorescence wavelength of the fluorophore is then measured and compared with a known value to determine extent of cure or extent of solidification.

The fluorophores of the invention undergo a large change in the electronic charge distribution upon absorption of light, and include compounds comprising substituted linear alkenes having an electron accepting group and an electron donating group. Preferably, the electron accepting group is attached at the alpha position and the electron donating group is attached at the omega position of the linear alkene. The electron accepting group is selected from the group consisting of 4-pyridinium alkylsulfonate, para-substituted phenyl, 1-naphthyl substituted at the 5-position, and 2-naphthyl substituted at the 6-position. The substituent of the para-substituted phenyl, 1-naphthyl and 2-naphthyl groups is selected from the group consisting of nitro, sulfoamido, sulfonate, cyano, acyl and carboxylic ester groups. The electron donating group is selected from the group consisting of 4-(N,N-dialkylanilino), 6-[2-(N,N-dialkylamino)naphthyl] and 1-[5-(N,N dialkylamino)naphthyl].

It is, therefore, an object of the present invention to provide a method of monitoring the extent of cure of a polymerizing material or the extent of solidification of a thermoplastic polymer by measuring change in peak fluorescence wavelength of a fluorophore.

It is another object of the present invention to provide a class of fluorophores which exhibit a relatively large change in peak fluorescence wavelength for use in the method of the invention.

It is another object of the invention to provide a class of fluorophores which absorb light in the visible range.

It is still another object of the invention to provide a device for use in connection with measuring change in peak fluorescence wavelength during the curing of a polymerizing material or the solidification of a thermoplastic polymer.

These and other objects of the present invention will become apparent from the detailed description to follow.

BRIEF DESCRIPTION OF THE DRAWINGS

There follows a detailed description of the preferred embodiments of the present invention which are to be taken together with the accompanying drawings, wherein.

DESCRIPTION OF THE PREFERRED EMBODIMENTS

According to the method of the invention, a trace amount of a fluorophore, i.e., typically 10 to 100 ppm by weight, is dissolved in a polymerizing material. Preferably, the fluorophore is selected from the class of fluorophores of the present invention, which are described in greater detail below. The change in peak fluorescence wavelength of the fluorophore is then measured during polymerization. The results are plotted as a function of cure time and a correlation is established between the wavelength shift and the extent of cure. Once this correlation is established, an absolute value for the extent of cure can be obtained from the measured value of the wavelength shift. Alternatively, the measured value of the wavelength shift can be used to compare or maintain the extent of cure throughout a manufacturing or clinical process. Thus, the method is especially advantageous for in situ, non-destructive cure monitoring because it eliminates the need for an internal standard fluorophore which is usually required in methods based on measurement of fluorescence intensity change. Further, the method does not require a complex optical system based on measurement of fluorescence anisotropy change.

The method of the invention is also useful for measurement of the extent of solidification (or cooling) of a thermoplastic polymer. The peak fluorescence wavelength of a fluorophore which is dissolved in a thermoplastic polymer decreases with decrease in the mobility of polymer segments (or the decrease in the free volume). Consequently, as the molten thermoplastic polymer cools and its segmental mobility decreases, the peak fluorescence wavelength of the fluorophore monotonically decreases. Therefore, once the calibration relationship between the peak fluorescence wavelength and the extent of solidification, as well as the onset of solidification, of the polymer is established by experiments, the peak fluorescence wavelength of the fluorophore can be measured during the processing of the polymer by injection molding to detect its solidification. Thus, measurement of peak fluorescence wavelength permits the adjustment of the injection molding cycle so that the mold is opened and the product ejected at optimum times. Opening the mold too soon will result in warping of the product shape, while allowing the product to remain in the mold too long will result in decreased productivity.

Figure 1:
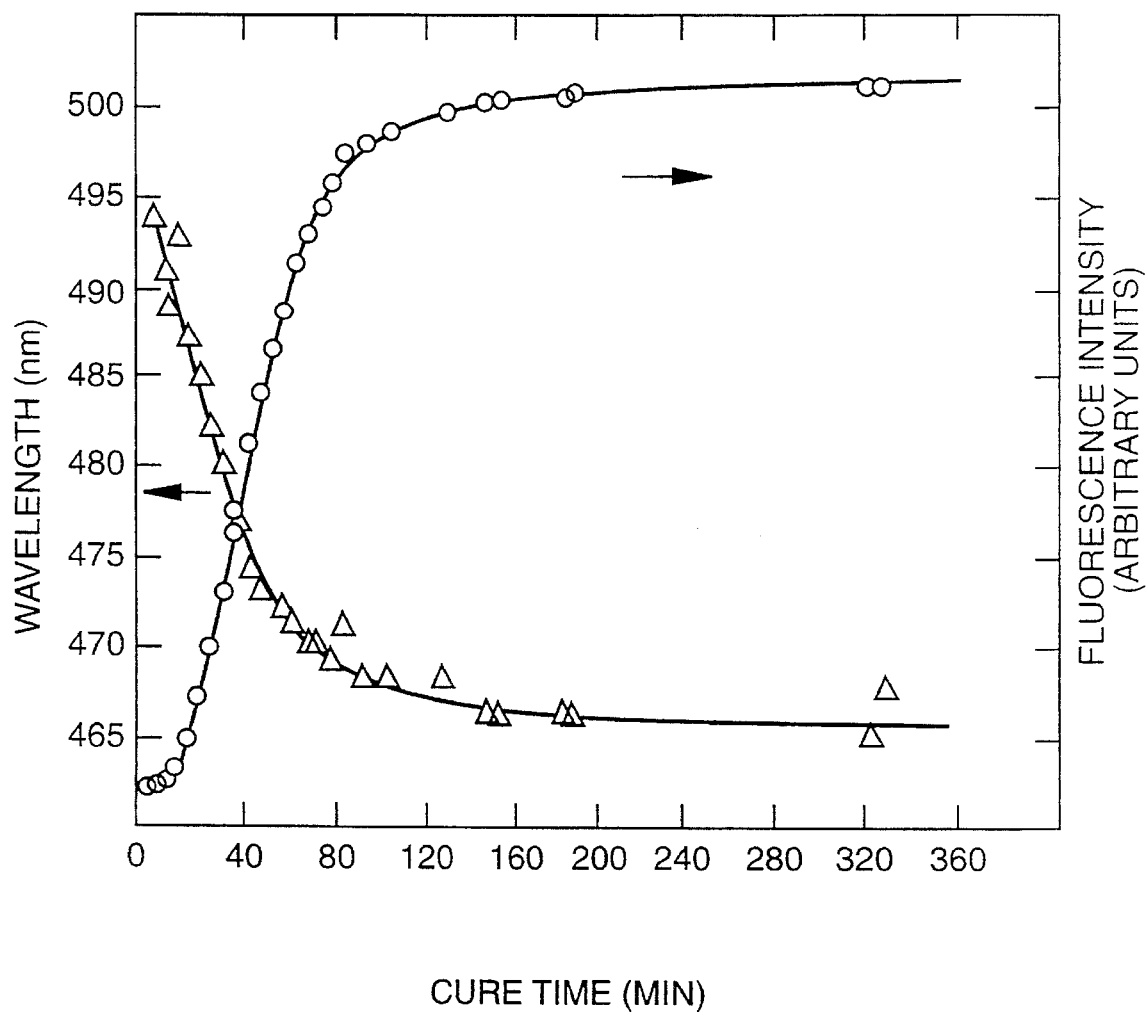
FIG. 1 shows a graph of peak fluorescence wavelength and fluorescence intensity versus cure time during the cure of DMA-DPH in a stoichiometric mixture of diglycidyl ether of bisphenol A ("DGEBA") and diethylene triamine ("DETA") at 50° C.

FIG. 1 shows the results of monitoring peak fluorescence wavelength of DMA-DPH in a stoichiometric mixture of diglycidyl ether of bisphenol A ("DGEBA") and diethylene triamine at 50° C. in accordance with the method of the invention. Specifically, the results are shown as a plot of peak fluorescence wavelength (triangles) and fluorescence intensity (circles) versus cure time. As is shown in the graph, peak fluorescence wavelength decreased rapidly and then decreased slowly after the cure time of 50 minutes. The peak fluorescence wavelength remained practically unchanged after the cure time of 160 minutes. The overall decrease in the peak fluorescence wavelength was 30 nm.

While the fluorophore DMA-DPH may be utilized, the fluorophores used in the method of the invention are preferably selected from the class of fluorophores of the invention, which include compounds comprising substituted linear alkenes having an electron accepting group and an electron donating group. Preferably, the electron accepting group is attached at the alpha position and the electron donating group is attached at the omega position of the linear alkene. The substituted linear alkenes include derivatives of ethylene, butadiene, hexatriene, and homologous higher conjugated linear alkenes. The electron accepting group is preferably one of the following groups: 4-pyridinium alkylsulfonate; and para-substituted phenyl, 1-naphthyl substituted at the 5-position and 2-naphthyl substituted at the 6-position, with the substituent groups chosen from the nitro, sulfoamido, sulfonate, cyano, acyl and carboxylic ester groups. The electron donating group is preferably one of the following: 4-(N,N-dialkylanilino), 6-[2-(N,N-dialkylamino)naphthyl] and 1-[5-(N,N-dialkylamino)naphthyl]. Among the most preferred fluorophores are the following:

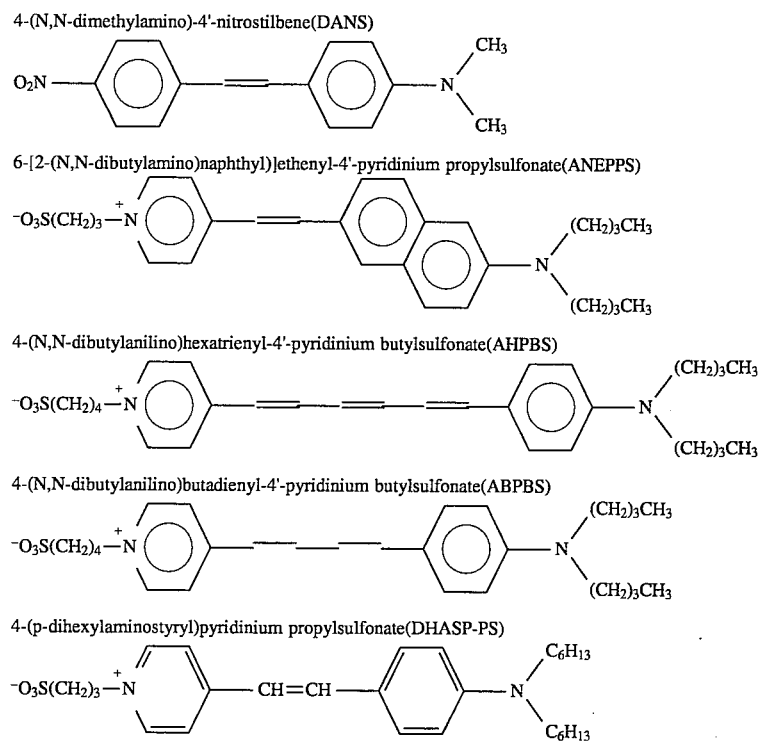

The wavelength-shift fluorophores of the invention exhibit a much larger change in the peak fluorescence wavelength than DMA-DPH. For example, the overall decrease in the peak fluorescence wavelength of DANS during the cure of a stoichiometric mixture of DGEBA and 4,4'-methylene-bis(cyclohexylamine) ("PACM") at 60° C. was 69 nm. The post-cure of 16 hours at 130° C. caused an additional decrease of 20 nm. The overall decrease of 69 nm was more than twice the overall decrease of 30 nm in the peak fluorescence wavelength of DMA-DPH during the cure at 50° C. of a similar epoxy resin which was a stoichiometric mixture of DGEBA and DETA.

Each of the wavelength-shift fluorophores of the invention also exhibits a much larger change in Stokes' shift than DMA-DPH in response to the change in polarity and mobility of its surroundings. Stokes' shift (the difference between the peak wavenumber of the absorption spectrum and the peak wavenumber of the fluorescence spectrum) provides a measure of the polarity and the mobility of the medium in which the fluorophore resides, and is discussed in Lin et al., 35 Polymer 687 (1994), which is herein incorporated by reference. Specifically, during the curing process, the electronic charge distribution, together with the dipole moment of a fluorophore, is substantially changed during an electronic transition to the excited state. After dissipation of intramolecular vibrational energy, the energy of the fluorophore molecules in the excited state is lowered by the reorientation of solvent molecules (or polymer segments) around the fluorophore molecules. The energy reduction due to solvent reorientation, together with the energy loss due to intramolecular vibrational relaxation, is observed as the Stokes' shift. For example, the overall decrease in the Stokes' shift of DANS during the cure of a stoichiometric mixture of DGEBA and PACM at 60° C. was 2349/cm. The post-cure of 16 hours at 130° C. caused an additional decrease of 638/cm. The overall decrease of 2349/cm in the Stokes' shift was nearly twice the overall decrease of 1200/cm in the Stokes' shift of DMA-DPH during the cure at 55° C. of a similar epoxy resin which was a stoichiometric mixture of DGEBA and DETA.

Further, the fluorophores of the invention all absorb light in the visible range, which is desirable when an optical fiber probe is used for measuring the extent of cure of a polymerizing material or the extent of solidification of a thermoplastic polymer (discussed in greater detail below in connection with FIGS. 2 and 3). By contrast, excitation wavelength of DMA-DPH is in the ultraviolet ("UV") range, making detection of the peak fluorescence wavelength or the Stokes' shift more difficult because of interference from impurity fluorescence of the resin and the optical fiber probe.

The shift in the peak fluorescence wavelength of each of the fluorophores of the invention, at the earlier stage of polymerization reactions, is increased by covalently attaching to the fluorophore molecules one or more moieties that take part in polymerization reactions, in such a manner that the photophysical properties of the fluorophore are not significantly altered by covalent bonding. This is accomplished using any one of the appropriate synthesis methods known in the art. For example, 4-(N-methacryloyloxymethyl-N-methylamino)-4'-nitrostilbene (hereinafter referred to as "methacryloxy-DANS") is formed by reaction of 4-(N-hydroxymethyl-N-methylamino)-4'-nitrostilbene with methacryl chloride. When dissolved in methyl methacrylate or methacrylic bone cements, methacryloxy-DANS shows a larger shift in the peak fluorescence wavelength than DANS at the earlier stage of polymerization. This is due to the fact that methacryloxy-DANS molecules continually become incorporated into growing polymer chains and respond to the polarity and mobility of the polymer chains (which are different from the polarity and mobility of unreacted monomer molecules), while DANS molecules remain in methyl methacrylate and respond only to methyl methacrylate molecules, until the later stage of polymerization. Similarly, increases in the shift of peak fluorescence wavelength at the earlier stage of polymerization, are obtained by using 4-(N, N-dimethacryloxymethylamino)-4'-nitrostilbene as a fluorophore instead of DANS to monitor the cure of dimethacrylic dental resins, or by using 4-(N,N-dihydroxymethylamino)-4'-nitrostilbene as a fluorophore instead of DANS to monitor the formation of polyurethanes or polyesters, or by using 4-(N,N-diaminomethylamino)-4'-nitrostilbene as a fluorophore instead of DANS to monitor the formation of polyureas or polyamides.

The wavelength-shift method and fluorophores of the invention are also useful for monitoring the polymerization of vinyl monomers at the later stage of cure. Monitoring and control of the later stages of a curing process are important in many manufacturing processes and clinical processes, such as the setting of bone cements. As an example, a trace amount of the fluorophore DHASP-PS was added to methyl methacrylate which contained 0.01M of the initiator azobisisobutyronitrile ("AIBN") at 55° C. At the cure time of 4.5 hours, when the extent of cure was 92%, the peak fluorescence wavelength of the fluorophore was 587 nm, only 5 nm shorter than the peak fluorescence wavelength of 592 nm at the beginning of the cure. However, after the cure time of 4.8 hours (when the peak fluorescence wavelength was 586 nm), the peak fluorescence wavelength decreased rapidly to 581 nm, 566 nm, and 555 nm at the cure times of 5.0 hours, 5.2 hours, and 5.5 hours, respectively.

Figure 2:
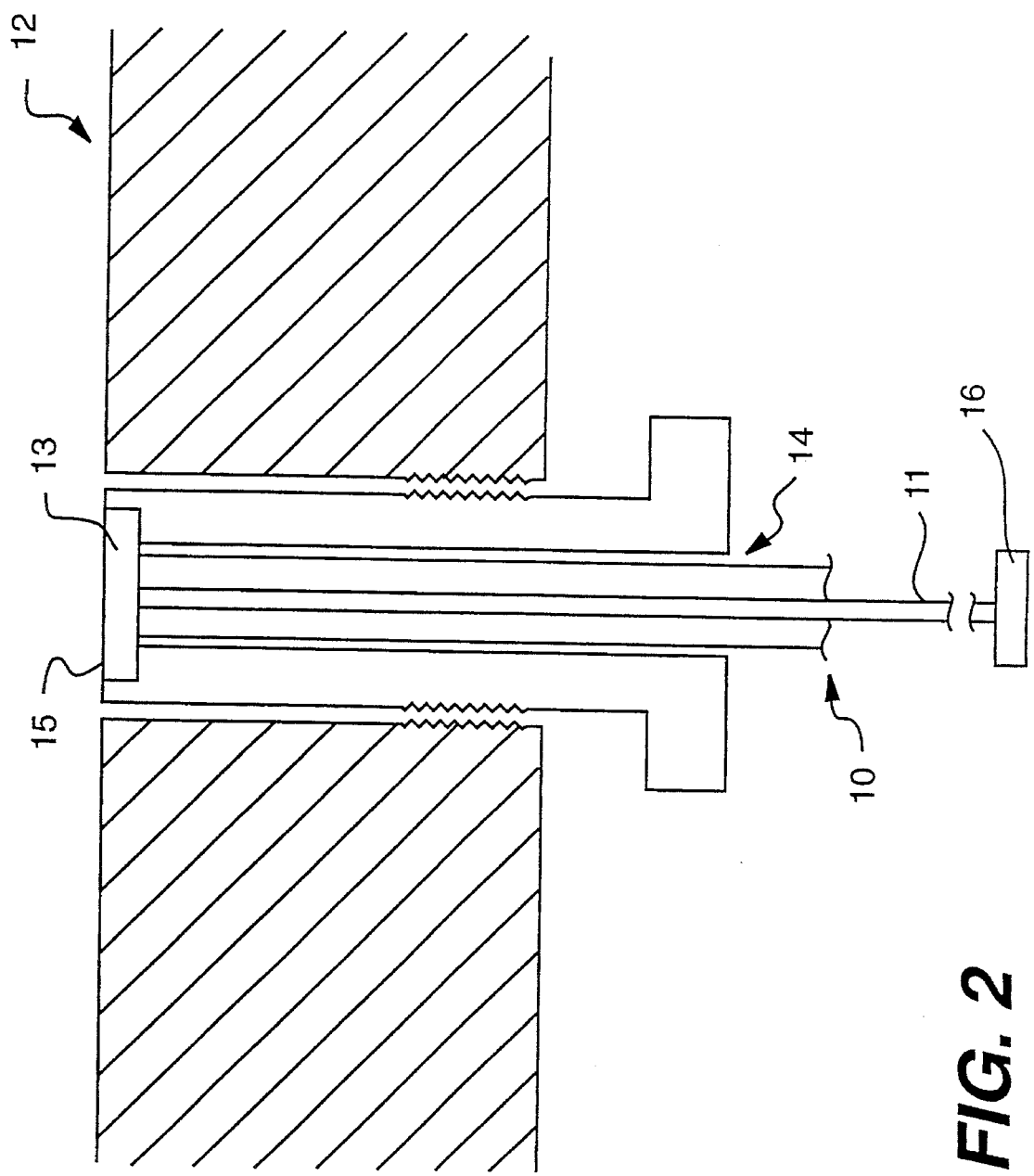
FIG. 2 shows a diagram of an optical fiber probe for use in conjunction with the method of the invention.
Figure 3:
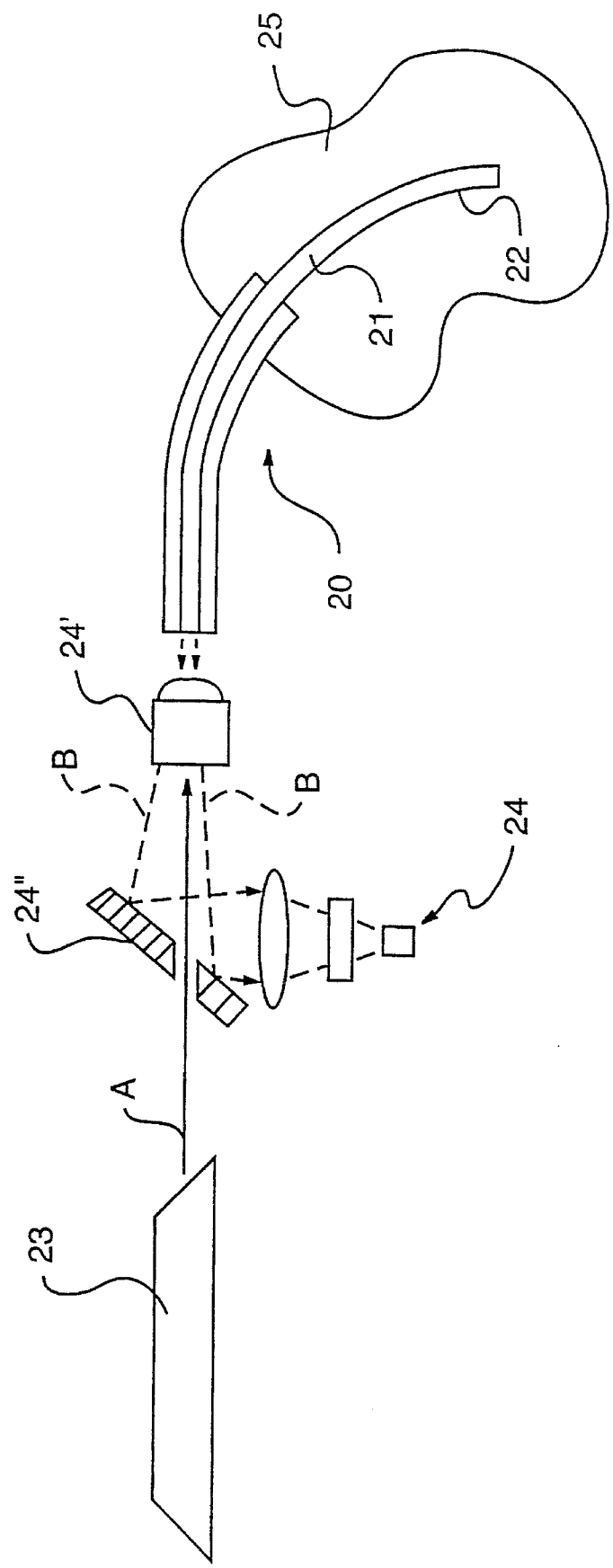
FIG. 3 shows a diagram of another optical fiber probe for use in conjunction with the method of the invention which utilizes evanescent waves to produce fluorescence emission.

FIG. 2 shows an example of a design of an optical fiber probe 10 for use in conjunction with the method of the invention. The probe 10 is inserted into a processing machine 12 in a port 14 normally used for a temperature or a pressure probe. The optical fiber probe 10 includes a bifurcated optical fiber that contains a bundle of nineteen fibers and a window 13. The central fiber 11 carries the excitation light of an appropriate wavelength from a light source 16 to the fluorophore molecules which are dissolved in the polymerizing material inside the processing machine 12. The collection fibers carry the fluorescence from the fluorophore molecules to the monochromator-detector (not shown) where peak wavelength is measured. The monochromator is a wavelength-dispersing component which disperses the polychromatic fluorescence radiation into light of various wavelengths. A fluorescence spectrum is obtained when the intensity of the light from the monochromator at various wavelengths is measured with the detector and plotted as a function of the wavelength. The peak fluorescence wavelength is determined as the wavelength at which the fluorescence intensity is a maximum.

Other probe configurations may also be utilized in the method of the invention. For example, the central fiber 11 can be replaced by a large number of excitation light fibers randomly distributed among a large number of collection fibers. FIG. 3 shows another example of an optical probe 20 which operates based on evanescent-wave induced fluorescence spectroscopy. This method is particularly useful in the manufacturing of polymer matrix composites. In this arrangement, an uncoated optical fiber 21 of high refractive index that is immersed or embedded in the polymerizing material 25 carries light (shown by arrow A) from a light source 23, such as an Argon laser, to the fluorophore molecules in the polymerizing material 25. Fluorescence emission from the fluorophore molecules, which are excited by evanescent waves penetrating shallowly beyond the fiber surface 22, enters the fiber 21 and is detected at the entrance end of the fiber 21 by a monochromator-detector 24 which utilizes an objective 24' and mirror 24" configuration to direct the fluorescence emission (shown by arrows B). Detection at the distal end of the fiber 21 is also possible as is known to those of ordinary skill in the art. Evanescent-wave excitation of fluorophore molecules provides distributed sensing so that the optical fiber probe 20 may provide a spatial profile of the measurand along the length of the fiber, which is sandwiched between layers of cloth prepregnated with a resin or placed within a preformed fibrous structure.

The fluorophores of the invention are especially useful when a probe configuration based on evanescent-wave induced fluorescence spectroscopy is used for cure monitoring. This is due to the fact that the fluorophores of the invention absorb visible light from the Argon ion laser, which is typically utilized in this configuration. As an example, DANS, ANEPPS, AHPBS, ABPBS, and DHASP-PS were each used to monitor the cure, at 60° C. for 100 minutes, of an epoxy resin that was a stoichiometric mixture of DGEBA and PACM. The wavelengths of light from an Argon ion laser for exciting DANS, ANEPPS, AHPBS, ABPBS, and DHASP-PS are 454 nm, 497 nm, 514 nm, 514 nm, and 488 nm, respectively. The values of the overall decrease in the peak fluorescence wavelength for DANS, ANEPPS, AHPBS, ABPBS, and DHASP-PS were 69 nm, 61 nm, 55 nm, 44 nm, and 37 nm, respectively. After the post-cure of 16 hours at 130° C., the values of the overall decrease (compared to the uncured resin) in the peak fluorescence wavelength for DANS, ANEPPS, AHPBS, ABPBS, and DHASP-PS were 89 nm, 68 nm, 62 nm, 50 nm, and 43 nm, respectively.

Although a wavelength-shift fluorophore is added to the polymerizing (or thermoplastic) material at very low concentrations (10 to 100 ppm by weight), the addition of a fluorophore is not practical in some cases, for example, when it discolors the products or when it is required in an excessive amount for large-sized products. In such cases, the fluorophore may be immobilized by covalent bonding on the surface 15 of the optic fiber probe's window 13 that is in contact with the polymerizing (or thermoplastic) material (FIG. 2) or, when evanescent-wave excitation is used, immobilized on the surface 22 of the uncoated optic fiber 21 (FIG. 3). For example, the glass or alumina surface 15 of the window 13 or the surface 22 of the uncoated optic fiber 21 is first modified by reaction with omega-isocyanatoalkyltriethoxysilane. The fluorophore 4-(N-hydroxymethyl-N-methylamino)-4'-nitrostilbene is then immobilized on the modified surface by reaction with the isocyanato group. Finally, the surface 15, 22 with the immobilized fluorophore molecules is conditioned before the use of the optic fiber probe 10, 20 by immersing the modified optic fiber 21 in the material 25 to be monitored or by coating the modified window surface 15 with a thin layer of the material to be monitored.

In one example of immobilization of a fluorophore by covalent bonding, glass fiber was silanized with the use of 3-aminopropyltriethoxy silane. A dansyl fluorophore was then covalently immobilized on the silanized glass fiber by the reaction of the silanized glass with 5-dimethylamino-1-sulfonyl chloride ("dansyl chloride"). The overall decrease in the peak fluorescence wavelength of the immobilized dansyl fluorophore during the cure of a stoichiometric mixture of DGEBA and PACM at 100° C. for one hour was 75 nm, indicating that the dansyl fluorophore was effective for cure monitoring of the epoxy resin even when it was covalently immobilized.

Alternatively, the fluorophore is immobilized by physical adsorption on the surface 15 of the optic fiber probe's window 13 that is in contact with the polymerizing (or thermoplastic) material or, when evanescent-wave excitation is used, on the surface 22 of the uncoated optic fiber 21. When it is desirable to increase the fluorescence intensity to facilitate the determination of the fluorescence peak, the number of the fluorophore molecules that are immobilized on the surface 15, 22 is increased by increasing the surface area of the window surface 15 or the surface 22 of the uncoated optic fiber 21. This is accomplished, for example, by coating the surface 15 or the uncoated optic fiber 21 with porous sol-gel glass, by attaching porous particles on the surface 15, 22 with a binder, or by attaching or fastening a thin, clear, porous disk on the surface 15 of the window that is in contact with the material being monitored. Finally, the surface 15, 22 with the immobilized fluorophore molecules is conditioned before the use of the optic fiber probe 10 or 20 by immersing the modified optic fiber 21 in the material to be monitored or by coating the modified window surface 15 with a thin layer of the material to be monitored.

In one example of immobilization of a fluorophore by physical adsorption, DHASP-PS was immobilized on a porous silica surface by adsorption. During the cure of a stoichiometric mixture of DGEBA and PACM at 60° C. for 1.75 hours, the peak fluorescence wavelength of the immobilized DHASP-PS fluorophore decreased from 590 nm to 565 nm, with a decrease of 25 nm, while the peak fluorescence wavelength of the same fluorophore dissolved in the same epoxy resin decreased from 593 to 555 nm, with a decrease of 38 nm. Thus, even when the DHASP-PS fluorophore was immobilized by physical adsorption, it was effective for cure monitoring of the epoxy resin.

Although the invention has been described in considerable detail with respect to preferred embodiments thereof, variations and modifications will be apparent to those skilled in the art without departing from the spirit and scope of the invention as set forth in the claims. Moreover, although the present disclosure focuses primarily on monitoring the extent of cure of a polymerizing material, it is to be understood that the method of the invention and class of fluorophores described herein are equally useful in connection with monitoring the extent of solidification of a thermoplastic polymer.

We claim:

1. A method of measuring extent of cure of a polymerizing material comprising the steps of:

selecting a polymerizing material;

selecting a wavelength-shift fluorophore;

dissolving said fluorophore in said polymerizing material;

measuring change in peak fluorescence wavelength of said fluorophore resulting from a change in polarity and mobility of the polymerizing material surrounding said fluorophore; and comparing said change with a known value to determine extent of cure of said polymerizing material.

2. The method according to claim 1 further comprising the step of attaching at least one moiety to said fluorophore before said step of dissolving, said moiety being selected from the group of reactive moieties of said polymerizing material.

3. The method according to claim 2 wherein said polymerizing material comprises methacrylate or methacrylic bone cement and said fluorophore after said step of attaching comprises 4-(N-methacryloyloxymethyl-N-methylamino)-4'-nitrostilbene.

4. The method according to claim 1 wherein said fluorophore comprises a substituted linear alkene having an electron accepting group and an electron donating group, said electron accepting group being selected from the group consisting of 4-pyridinium alkylsulfonate, para-substituted phenyl, 1-naphthyl substituted at the 5-position and 2-naphthyl substituted at the 6-position, said electron donating group being selected from the group consisting of 4-(N,N-dialkylanilino), 6-[2-(N,N-dialkylamino)naphthyl] and 1-[5-(N,N-dialkylamino)naphthyl].

5. The method according to claim 4 wherein said fluorophore is selected from the group consisting of: 4-(N,N-dimethylamino)-4'-nitrostilbene, 6-[2-(N,N-dibutylamino)naphthyl]ethenyl-4'-pyridinium propylsulfonate, 4-(N,N-dibutylanilino)hexatrienyl-4'-pyridinium butylsulfonate, 4-(N,N-dibutylanilino)butadienyl-4'-pyridinium butylsulfonate, and 4-(p-dihexylaminostryryl)pyridinium propylsulfonate.

6. A method of measuring extent of solidification of a thermoplastic polymer comprising the steps of:

dissolving a fluorophore in a thermoplastic polymer;

measuring change in peak fluorescence wavelength of said fluorophore resulting from a change in polarity and mobility of the thermoplastic polymer surrounding said fluorophore; and comparing said change with a known value to determine extent of solidification of said thermoplastic polymer.

7. The method according to claim 1 wherein said fluorophore comprises a substituted linear alkene having an electron accepting group and an electron donating group, said electron accepting group being selected from the group consisting of 4-pyridinium alkylsulfonate, para-substituted phenyl, 1-naphthyl substituted at the 5-position and 2-naphthyl substituted at the 6-position, said electron donating group being selected from the group consisting of 4-(N,N-dialkylanilino), 6-[2-(N,N-dialkylamino)naphthyl] and 1-[5-(N,N-dialkylamino)naphthyl].

8. The method according to claim 7 wherein said fluorophore is selected from the group consisting of: 4-(N,N-dimethylamino)-4'-nitrostilbene, 6-[2-(N,N-dibutylamino)naphthyl]ethenyl-4'-pyridinium propylsulfonate, 4-(N,N-dibutylanilino)hexatrienyl-4'-pyridinium butylsulfonate, 4-(N,N-dibutylanilino)butadienyl-4'-pyridinium butylsulfonate, and 4-(p-dihexylaminostryryl)pyridinium propylsulfonate.

9. A device for monitoring degree of cure of a polymerizing material or extent of solidification of a thermoplastic polymer comprising:

a light source for producing excitation light;

an optical fiber probe for carrying the excitation light from the light source to fluorophore molecules immobilized on a surface of said optical fiber probe; and means for detecting and measuring peak fluorescence wavelength of said immobilized fluorophore molecules when said optical fiber probe is contacted with a polymerizing material or a thermoplastic polymer.

10. The device according to claim 9 wherein said optical fiber probe generates evanescent-wave excitation.

11. The device according to claim 9 wherein said fluorophore is immobilized by covalent bonding.

12. The device according to claim 9 wherein said fluorophore is immobilized by physical adsorption.

13. A method of monitoring degree of cure of a polymerizing material or degree of solidification of a thermoplastic polymer comprising:

contacting an optical fiber probe having immobilized fluorophore molecules thereon with a polymerizing material or a thermoplastic polymer;

producing excitation light by means of a light source;

carrying the excitation light from the light source to said immobilized fluorophore molecules by means of said optical fiber probe; and measuring peak fluorescence wavelength of said immobilized fluorophore molecules.

14. The method according to claim 13 further comprising the step of immobilizing said fluorophore molecules on said optical fiber probe by physically adsorbing said fluorophore on said optical fiber probe.

15. The method according to claim 13 further comprising the step of covalently bonding said fluorophore molecules on said optical fiber probe before said step of contacting.

16. The method according to claim 15 wherein said step of covalently bonding comprises modifying a surface of the optical fiber probe by reaction with omega-isocyanatoalkyltriethoxysilane, immobilizing a fluorophore on said modified surface, and coating said modified surface with a layer of said polymerizing material or thermoplastic polymer.

* * * * *